United States Patent [19]

Leon et al.

[11] 4,338,395
[45] Jul. 6, 1982

[54] METHOD FOR THE ANALYSIS OF TRIGLYCERIDES

[75] Inventors: Luis P. León, Fairfield, Conn.; Chien-Kuo Yeh, Pleasantville; Syed I. Ahmad, Orangeburg, both of N.Y.

[73] Assignee: Technicon Instruments Corporation, Tarrytown, N.Y.

[21] Appl. No.: 171,112

[22] Filed: Jul. 21, 1980

[51] Int. Cl.$^3$ .......................... C12Q 1/50; C12Q 1/48
[52] U.S. Cl. ........................................ 435/17; 435/15; 435/18; 435/26; 435/176; 435/180
[58] Field of Search .................................. 435/15–19, 435/26, 175–182, 291

[56] References Cited

U.S. PATENT DOCUMENTS

| | | | |
|---|---|---|---|
| 3,579,454 | 5/1971 | Collier | 435/263 |
| 3,703,591 | 11/1972 | Bucolo et al. | 435/15 |
| 3,926,736 | 12/1975 | Bucolo | 435/26 |
| 4,019,961 | 4/1977 | Klose et al. | 435/15 |
| 4,056,442 | 11/1977 | Huang et al. | 435/15 |
| 4,061,141 | 12/1977 | Hyden et al. | 435/179 |
| 4,066,508 | 1/1978 | Rauscher et al. | 435/15 |
| 4,080,263 | 3/1978 | Bernt et al. | 435/26 |
| 4,179,334 | 12/1979 | Esders et al. | 435/15 |
| 4,242,446 | 12/1980 | Madappally et al. | 435/15 |
| 4,259,440 | 3/1981 | Gupta et al. | 435/15 |

Primary Examiner—Peter A. Hruskoci
Attorney, Agent, or Firm—Morgan, Finnegan, Pine, Foley & Lee

[57] ABSTRACT

Method of analyzing for triglycerides in a biological fluid is disclosed which eliminates interferences arising from endogenous glycerol and pyruvate and the need for parallel blank correction.

28 Claims, 1 Drawing Figure

METHOD FOR THE ANALYSIS OF TRIGLYCERIDES

BACKGROUND OF THE INVENTION

This invention relates generally to an analytical enzymatic determination of serum triglycerides. More specifically, it relates to a method which incorporates a sequential and/or simultaneous sample pretreatment which eliminates endogenous glycerol and pyruvate interferences and the need for blank correction and a triglyceride assay which employs immobilized enzymes for the detection reaction.

SUMMARY OF THE INVENTION

In accordance with this invention, there is disclosed a method for the analysis of triglycerides in a biological fluid which comprises:

(a) treating said biological fluid to remove endogenous glycerol and pyruvate by combining with said fluid, as a first component, adenosine triphosphate (ATP), enzyme glycerolkinase (GK) and a metal cation activator for said GK, as a second component, enzyme pyruvate kinase (PK) in the presence of substrate phosphoenol pyruvate (PEP) and an enzyme PK activator, and as a third component, glutamate and enzyme alanine aminotransferase (GPT).

(b) enzymatically hydrolyzing the triglycerides in the resulting fluid free of glycerol and pyruvate by combining said fluid with a mixture comprised of a microbial lipase and a surfactant; and (c) determining the amount of glycerol produced from said enzymatic hydrolysis.

DETAILED DESCRIPTION OF THE INVENTION

The method disclosed and claimed herein is a procedure used for the analysis of triglycerides in biological fluids, especially body fluids such as serum.

In general, the procedure involves pretreating a serum sample to remove interferences arising from endogenous glycerol and pyruvate, quantifying the glycerol produced by enzymatic hydrolysis by employment of an immobilized enzyme coil.

The novel procedure claimed herein advantageously eliminates the need for parallel blank correction, the latter step required in prior art methods.

In the method as claimed herein, the removal of glycerol and pyruvate interferences endogenous to the biological fluid is accomplished pursuant to the following reaction scheme:

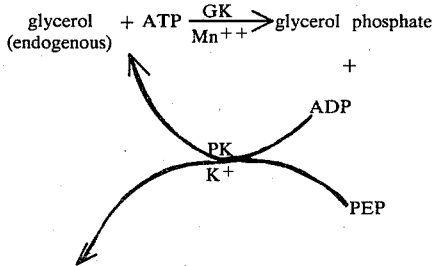

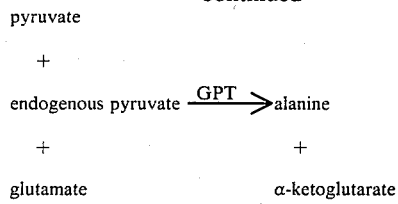

-continued

In the above given reaction-scheme, ATP is adenosine triphosphate, ADP is adenosine diphosphate, PEP is phosphoenol pyruvate. In the above given reactions, the amount of endogenic glycerol is completely converted to the phosphorilated form by the action of a specific kinase, e.g., glycerol kinase (GK). The phosphorilated glycerol is a non-interference in the new method. The ADP produced in recycled back to ATP under the influence of a specific kinase, e.g. pyruvate kinase (PK), and in the presence of PEP. This latter reaction is needed to eliminate the ADP which will interfere in the accurate quantitation of triglycerides (TG). In the above given reaction-scheme, the endogenic pyruvate pulse the pyruvate produced in the previous reaction and in the presence of glutamate are transformed to alanine and α-ketoglutarate produced in this reaction as non-interferences in the TG quantitation. In the above given reaction scheme, it is necessary to stop the enzyme activity of the specific kinase (1) acting upon endogenous glycerol. This kinase reaction is stopped after all the endogenous glycerol has been transformed to glycerol-phosphate. Failure to stop the specific kinase (1) activity will result in the conversion of glycerol (produced by lipolysis) to glycerol-1-phosphate with concomitant production of ADP. There are two general approaches to stop the specific kinase (1) activity:

(a) A metal chelating compound is used to sequestrate the specific metal ion used to activate the specific kinase (1). Once the metal ion is chelated (e.g., by EDTA) the kinase (1) is completely rendered inactive.

(b) In the above given reaction scheme all three specific enzymes [kinase (1), kinase (2) and other specific enzymes] can be either free in solution or immobilized form.

In the case where the enzymes are immobilized there is no need to chemically stop the kinase (1) activity. This enzyme is physically attached to the inner wall of a plastic (nylon) coil and thus the enzyme does not enter into the lipolysis reaction.

For the above given reaction scheme the preferred formulations are as follows:

REAGENT NO. 1

This reagent contains glycerol kinase, pyruvate kinase, alanine aminotransferase and ATP. The reagent also contains a buffer system and required enzyme activators. Other reagent formulations were investigated and were found to give equivalent results. Table No. 1 illustrates the enzymes and substrates which could be used as replacements for the specific kinase (2) reaction.

TABLE NO. 1

| Enzyme | Substrate |
| --- | --- |
| Acetyl Kinase | Acetyl Phosphate |
| Creatine Kinase | Creatine Phosphate |

TABLE NO. 1-continued

| Enzyme | Substrate |
|---|---|
| 3-Phosphoglycerate Kinase | Glycerate 1,3-Diphosphate |

REAGENT NO. 2

This reagent is used to stop the activity of the kinase (1) as discussed in approach (2) above.

The reagent responsible for the enzymatic hydrolysis of triglycerides comprises a coactive mixture of microbial lipase (e.g., Candida Cylindracea) a surfactant (polyoxyethylene alkanolamides) and Ca Cl$_2$. All three components are essential for complete hydrolysis. More specifically, the microbial lipase is obtained from a culture broad of Candida Cylindracea. Such Candida lipase should have an activity within the range of 40,000 u/1.–1,000,000 u/1. (reaction mix). Other Candida lipases were found to give equivalent results when used in combination with the surfactant and Ca Cl$_2$.

As indicated above a surfactant is an essential component of the triglycerides-hydrolysis mixture. While we preferred to use a surfactant belonging to the nonionic group of polyoxyethylene alkanolamides, surfactants pertaining to the following nonionic groups were also found to give equivalent results:
1. Polyoxyethylene (POE) ester of fatty acids
2. POE mercaptans
3. POE Alkylamides
4. POE Alkylamines
5. POE Polyol esters
6. POE Acetylenic glycols
7. POE Phosphate esters The general reaction sequences for the quantitation of glycerol produced by lipolysis is summarized by the following reaction scheme:

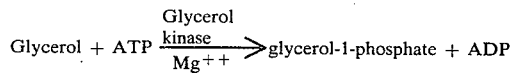

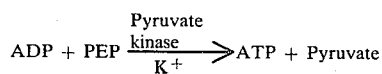

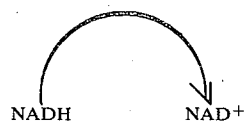

In the above given scheme the glycerol produced by lipolysis is dialyzed into a buffered reagent containing PEP, ATP Mg$^{++}$ and NADH. The glycerol kinase, pyruvate kinase and lactate dehydrogenase (LDH) reactions take place inside the immobilized enzyme coil (see flow diagram above) where the three latter enzymes are bound to the inner wall of a nylon tubing. Also, inside the immobilized enzyme coil NADH is oxidized to NAD. The decrease in absorbance of NADH to NAD is directly proportional to the amount of glycerol produced in the lipolysis step.

BRIEF DESCRIPTION OF THE DRAWING

The FIGURE represents a schematic flow sheet of the continuous system or apparatus according to the present invention for the analysis of triglycerides in a biological fluid.

DETAILED DESCRIPTION OF THE DRAWING

Figure 1:
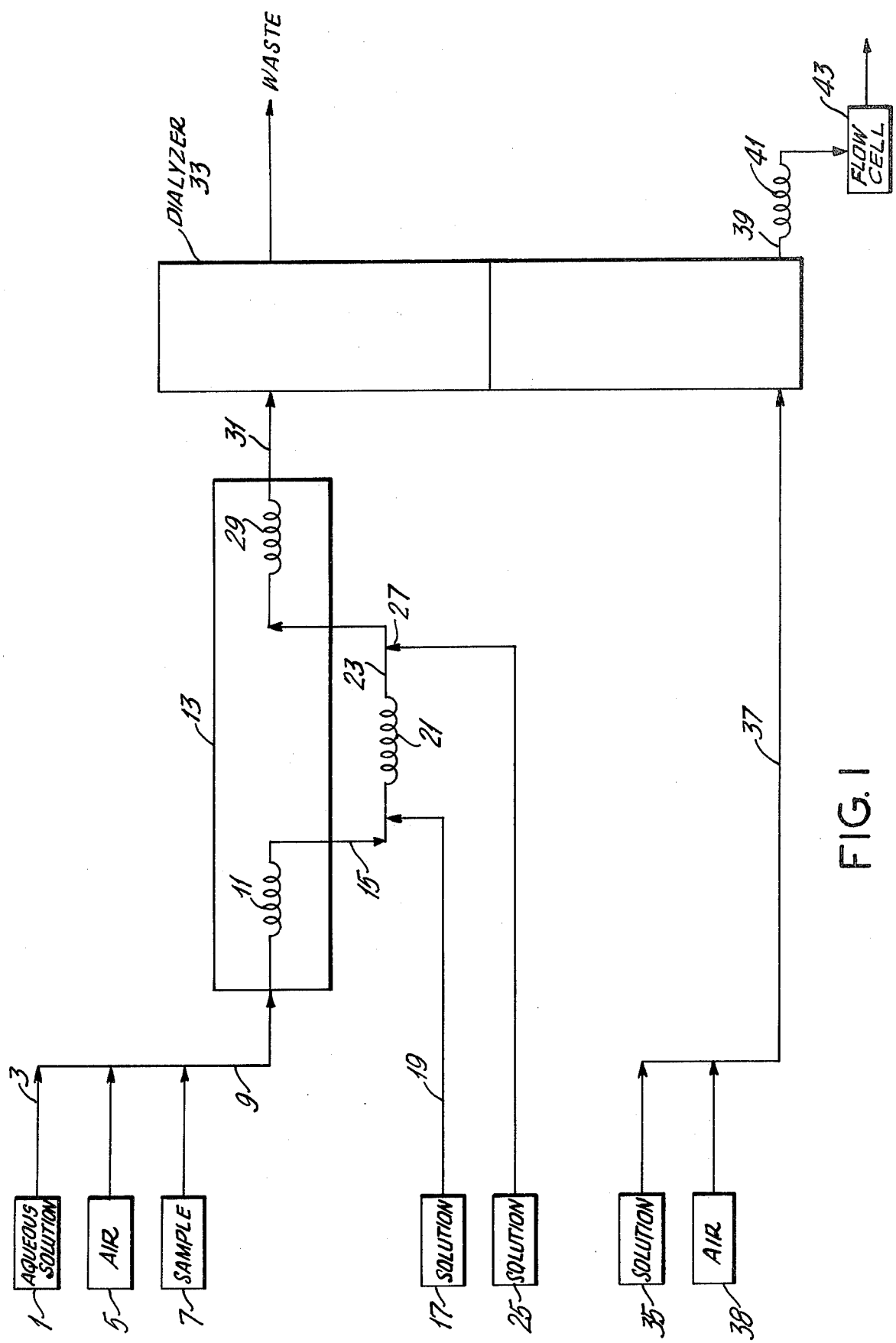

To illustrate one embodiment of the present invention for the analysis of triglycerides in a biological fluid, reference is made to the FIGURE. The FIGURE illustrates a continuous system for the analysis of triglycerides.

An aqueous solution 1 which contains GK, PK, GPT, ATP, glutamate, PEP, Mn$^{++}$ and K$^+$ is pumped into conduit 3 where air 5 is added followed by sample 7. The mixed solution is conveyed via line 9 and passesd through coil 11 in heating bath 13 which is maintained at a temperature of about between 30° C. and 50° C. Coil 11 may be fabricated of a plastic material such as nylon, polyethylene, polyvinyl chloride, polystyrene, etc. or aluminum, glass, stainless steel or silicon rubber. Nylon is preferred. As the solution passes through coil 11, removal of endogenous glycerol and pyruvate occurs. The treated solution is conveyed via line 15 where solution 17 containing EDTA and surfactant are pumped via line 19 and combines with the solution which then flows through coil 21 which is at ambient temperature. On passing through coil 21, enzyme GK is inactivated. After the solution passes through coil 21 it is conveyed via line 23 and is combined with a solution 25 containing microbial lipases and a surfactant at 27. The combined solution is then passed through coil 29 in heating bath 13 where enzymatic hydrolysis occurs. The resulting solution is conveyed via line 31 to dialyzer 33 where the dialyzed solution is conveyed to the bottom portion of the dialyzer and combined with solution 35 which contains NADH and Mg$^{++}$ in solution via line 37 to which air 38 is also conveyed. The resulting solution is conveyed via line 39 to coil 41 where enzymes glycerol kinase (GK), pyruvate kinase (PK) and lactate dehydrogenase (LDH) are immobilized. After passing through coil 41, the resulting solution is photometrically scanned at 340 nm in flowcell 43.

In another embodiment of this invention, the above system is modified so that coil 11 contains immobilized enzyme GK. In this embodiment, no EDTA is necessary. As to other embodiments, coil 11 may also contain immobilized enzyme PK and/or immobilized enzyme GPT.

EXAMPLE I

The following procedure illustrates one manner of carrying out this invention in a continuous manner as in the Technicon ™ AutoAnalyzer ™ biochemical analyzer as described in U.S. Pat. No. 2,797,149.

The human serum sample (0.020–0.028 ml.) is combined with reagent No. 1 which contains glycerol kinase (50–200 units/dl.), ATP (5–16.5 mM.), MnCl$_2$ (1–20 mM.), pyruvate kinase (50–1000 units/dl.), PEP (5–16 mM.), CaCl$_2$ (30–60 mM.), GPT (50–500 units/dl.), glutamate (50–30 mM.) and tris buffer (50–100 mM, pH 7.6).

After mixing for ½ to 2 minutes at approximately 30° to 50° C., to the resultant solution is added reagent No. 2 which contains EDTA (40–80 mM.), 5-POE-lauricamide (7–15 g./l.) and tris buffer (50–100 mM., pH 7.5). After mixing for 10–60 seconds at room temperature, to the resulting solution is added reagent No. 3 which contains lipase (100,000–2,000,000 units/1.), bovine serum albumin (0.1–2 g/dl.), CaCl$_2$ (40–200 mM), and maleate buffer (50–100 mM, pH 6).

After mixing for 1–10 minutes at approximately 30°–50° C., the resulting solution is dialyzed across a dialyzer block equipped with a semi-permeable membrane.

The dialyzed glycerol is combined with an aqueous buffer solution of pH 7.8 which contains reduced nicotinamideadeninedinucleotide (NADH) (70–140 mg/l.), MgSO$_4$ (2–6 mM) and KCl (20–60 mM) and this solution is passed through an immobilized enzyme coil to which is physically bound GK, PK and LDH. After passing through the coil, the decrease of the NADH absorbance is monitored at 340 nm.

EXAMPLE II

The procedure of Example I is repeated except that only enzyme GK is immobilized. In this procedure no EDTA is used.

EXAMPLE III

The procedure of Example I is repeated except that MgCl$_2$ is used in place of MnCl$_2$.

EXAMPLE IV

The procedure of Example II is repeated wherein enzyme PK is employed along with GK in immobilized nylon coil form.

EXAMPLE V

The procedure of Example II is repeated except that enzyme GPT is employed along with enzyme GK in immobilized nylon coil form.

EXAMPLE VI

The procedure of Example I is repeated except that the following surfactants are used in place of POE-5 lauric acid:
POE-5 cocoamide
15-POE cocoamine

EXAMPLE VII

The procedure of Example I is repeated except that the following enzymes are used in place of GK:
glycerol dehydrogenase
glycerol oxidase In this procedure, the above enzymes together with enzyme GPT are in immobilized form in the same coil. No enzyme PK is necessary.

EXAMPLE VIII

The procedure of Example II is repeated wherein in place of the PEP-PK system, the following substrate-enzyme systems, as a second component are used:
acetyl phosphate-acetyl kinase
creatine phosphate-creatine kinase
glycerate 1,3-diphosphate-3-phosphoglycerate kinase It should be understood by those skilled in the art that various modifications may be made in the present invention without departing from the spirit and scope thereof as described in the specification and defined in the appended claims.

What is claimed is:

1. A method for the analysis of triglycerides in a biological fluid which comprises:
   (a) treating said biological fluid to remove endogenous glycerol and pyruvate by combining with said fluid, as a first component, adenosine triphosphate (ATP), enzyme glycerol kinase (GK) and a metal cation activator for said GK, as a second component, enzyme pyruvate kinase (PK) in the presence of substrate phosphoenol pyruvate (PEP) and an enzyme PK activator, and as a third component, glutamate and enzyme alanine aminotransferase (GPT);
   (b) enzymatically hydrolyzing the triglycerides in the resulting fluid free of glycerol and pyruvate by combining said fluid with a mixture comprised of a microbial lipase, a surfactant selected from polyoxyethylene (POE) alkylamides, POE esters of fatty acids, POE mercaptans, POE alkylamines, POE polyol esters, POE acetylenic glycols and POE phosphate esters, and an alkaline earth metal cation, in the form of a salt; and
   (c) determining the amount of glycerol produced from said enzymatic hydrolysis.

2. The method of claim 1 wherein said metal cation activator for said enzyme GK is selected from Mn$^{++}$ or Mg$^{++}$ provided in the form of a salt.

3. The method of claim 2 wherein said metal cation is Mn$^{++}$.

4. The method of claim 1 wherein said enzyme PK activator is potassium ion (K$^+$) provided in the form of a salt.

5. The method of claim 1 wherein said alkaline earth metal cation is calcium.

6. The method of claim 1 wherein said enzymes GK, PK and GPT are employed free in solution and further comprising the step subsequent to step (a) of deactivating said GK metal cation activator by adding a metal chelating compound.

7. The method of claim 6 wherein said metal chelating compound is ethylenediamine tetraacetic acid (EDTA).

8. The method of claim 1 wherein said enzyme GK is employed in immobilized form in which said enzyme is physically attached to the inner wall of a coil through which the fluid passes and contacts, and said other enzymes PK and GPT are optionally immobilized on the same coil.

9. The method of claim 8 wherein said coil is composed of a material selected from the group consisting of a plastic selected from nylon, polyethylene, polyvinyl chloride or polystyrene; aluminum, glass, stainless steel and silicon rubber.

10. The method of claim 9 wherein said coil is made of nylon.

11. The method of claim 8 wherein said glycerol determination comprises dialyzing the reaction product from said enzymatic hydrolysis into a buffered reagent comprising PEP, ATP, magnesium ion in the form of a salt, and NADH and passing said dialyzed solution through an immobilized enzyme coil to which is physically bound enzymes glycerol kinase (GK), pyruvate kinase (PK) and lactate dehydrogenase (LDH) and photometrically measuring at 340 nm the decrease in absorbance of NADH to NAD.

12. The method of claim 11 wherein said plastic coil and said immobilized enzyme coil are made of nylon.

13. The method of claim 1 wherein said microbial lipase is a *Candida lipase*.

14. The method of claim 13 wherein said *Candida lipase* is a Candida Cylindracea having an activity in the range of 40,000 u/l. to 1,000,000 u/l.

15. The method of claim 1 wherein said surfactant is a POE alkylamide.

16. The method of claim 15 wherein said surfactant is selected from POE-5-lauricamide or POE-5-cocoamide.

17. The method of claim 1 wherein said glycerol determination comprises dialyzing the reaction product from said enzymatic hydrolysis into a buffered reagent comprising PEP, ATP, magnesium ion in the form of a salt, and NADH and passing said dialyzed solution through an immobilized enzyme coil to which is physically bound enzymes glycerol kinase (GK), pyruvate kinase (PK) and lactate dehydrogenase (LDH) and photometrically measuring at 340 nm the decrease in absorbance of NADH to NAD.

18. The method of claim 17 wherein said coil is made of nylon.

19. In a method for the analysis of triglycerides in a biological fluid by pretreating said biological fluid to remove interferences arising from endogenous glycerol and pyruvate, enzymatically hydrolyzing the triglycerides in the resulting fluid and determining the amount of glycerol produced by said enzymatic hydrolysis, the improvement which comprises enzymatically hydrolyzing the triglycerides in the resulting fluid free of glycerol and pyruvate by combining said fluid with a mixture comprised of a microbial lipase, a surfactant selected from polyoxyethylene (POE) alkylamides, POE esters of fatty acids, POE mercaptans, POE alkylamines, POE polyol esters, POE acetylenic glycols and POE phosphate esters, and an alkaline earth metal cation, in the form of a salt.

20. The method of claim 19 wherein said microbial lipase is a *Candida lipase*.

21. The method of claim 19 wherein said *Candida lipase* is Candida Cylindracea having an activity in the range of 40,000 u/l to 1,000,000 u/l.

22. The method of claim 19 wherein said surfactant is a POE alkylamide.

23. The method of claim 22 wherein said surfactant is selected from POE-5-lauricamide or POE-5-cocoamide.

24. The method of claim 19 wherein said alkaline earth metal cation is calcium.

25. The method of claim 19 further comprising the improvement of determining the amount of glycerol produced by said enzymatic hydrolysis by measuring the decrease in absorbance resulting from the oxidative conversion of NADH to NAD.

26. The method of claim 25 wherein said oxidative conversion is effected by dialyzing the reaction product from the enzymatic hydrolysis into a buffered reagent comprising PEP, ATP, magnesium ion in the form of a salt, and NADH and passing said dialyzed solution through an immobilized enzyme coil to which is physically bound enzymes glycerol kinase (GK), pyruvate kinase (PK) and lactate dehydrogenase (LDH) and photometrically measuring at 340 nm the decrease in absorbance.

27. The method of claim 19 wherein said pretreatment employs a substrate-enzyme system selected from acetyl phosphateacetyl kinase, creatine phosphate-creatine kinase or glycerate 1,3-diphosphate-3-phosphoglycerate kinase.

28. The method of claim 19 wherein said pretreatment employs an enzyme selected from glycerol dehydrogenase or glycerol oxidase.

* * * * *